United States Patent [19]
Frechet et al.

[11] Patent Number: 5,728,457
[45] Date of Patent: Mar. 17, 1998

[54] POROUS POLYMERIC MATERIAL WITH GRADIENTS

[75] Inventors: Jean Frechet; Frantisek Svec, both of Ithaca, N.Y.

[73] Assignee: Cornell Research Foundation, Inc., Ithaca, N.Y.

[21] Appl. No.: 661,838

[22] Filed: Jun. 11, 1996

Related U.S. Application Data

[63] Continuation of Ser. No. 316,523, Sep. 30, 1994, abandoned.
[51] Int. Cl.[6] .................. B32B 5/14; B01D 15/08
[52] U.S. Cl. ............... 428/310.5; 210/635; 210/656; 210/198.2; 210/502.1
[58] Field of Search ............... 428/310.5, 304.4, 428/318.4, 319.3, 500; 210/635, 656, 198.2, 502.1, 300.34, 500.42; 95/88; 96/101

[56] References Cited

U.S. PATENT DOCUMENTS

| | | | |
|---|---|---|---|
| 3,598,728 | 8/1971 | Bixler | 210/198.2 |
| 3,796,657 | 3/1974 | Pretorius | 210/198.2 |
| 3,808,125 | 4/1974 | Good | 210/198.2 |
| 3,878,092 | 4/1975 | Fuller | 210/198.2 |
| 3,954,608 | 5/1976 | Valentin | 210/198.2 |
| 4,486,311 | 12/1984 | Nakajima | 210/635 |
| 4,863,647 | 9/1989 | Baylor, Jr. | 264/22 |
| 4,889,632 | 12/1989 | Svec | 210/500.28 |
| 4,923,610 | 5/1990 | Svec | 210/637 |
| 4,952,349 | 8/1990 | Svec | 264/45.1 |
| 5,135,627 | 8/1992 | Soane | 204/182.8 |
| 5,236,588 | 8/1993 | Zhang et al. | 210/500.35 |
| 5,334,310 | 8/1994 | Frechet | 210/198.2 |

FOREIGN PATENT DOCUMENTS

| | | | |
|---|---|---|---|
| 68 03 759 | 9/1968 | Netherlands | 210/198.2 |
| 1 118 736 | 3/1968 | United Kingdom | 210/198.2 |
| 6090 07965 | 7/1990 | WIPO | 210/198.2 |

OTHER PUBLICATIONS

Haerten, "High Performance Liquid Chromatography on Continuous Polymer Beds" Journal of Chromatography, 473 (1981) pp. 273–275.

*Primary Examiner*—Ernest G. Therkorn
*Attorney, Agent, or Firm*—Bruce F. Jacobs

[57] ABSTRACT

Porous polymeric matrix materials in the form of an integral body having a property gradient selected from any of pore size distribution, chemical composition or a combination thereof are disclosed along with a process for making the same.

12 Claims, 5 Drawing Sheets

POROUS POLYMERIC MATERIAL WITH GRADIENTS

This application is a continuation of application Ser. No. 08/316,523 filed on Sep. 30, 1994 now abandoned.

STATEMENT OF GOVERNMENT RIGHTS

This invention was made with government support under Grant No. A58-8304 awarded by the National Institutes of Health. The government has certain rights in the invention.

BACKGROUND OF THE INVENTION

Macroporous polymers are characterized by a rigid porous matrix that persists even in the dry state. These polymers are most frequently produced in the shape of regular beads by a suspension polymerization process. In this process, the polymerization mixture must contain both a crosslinking monomer and an inert diluent, the porogen (poor solvent for polymer). Porogens can be solvating or non-solvating solvents for the polymer that is formed, or soluble polymers, or mixtures thereof.

The pore size distribution of a porous polymer may cover a broad range of pore sizes from a few up to several hundred nanometers. Pores with a diameter of less than 2 nm are classified as micropores, pores ranging from 2 to 50 nm are classified as mesopores and pores over 50 nm are considered macropores. The larger the pores, the smaller the surface area of the pores. Therefore, porous polymers with very large pores have relatively low specific surface areas, typically much less than 10 $m^2/g$.

The morphology of macroporous polymers is rather complex. Macroporous polymers comprise interconnected microspheres (globules) that are partly aggregated in larger clusters that form the body of the beads. The size of the spherical globules that form the bulk of the macroporous polymer ranges from about 10 to about 50 nm. The pores in the macroporous polymer are irregular voids between clusters of the globules (macropores), between globules within each cluster (mesopores) and within the globules themselves (micropores). The pore size distribution reflects the internal organization of both the globules and their clusters within the macroporous polymer and depends on the composition of the polymerization mixture and reaction conditions. The most effective variables that control pore size distribution are the percentage of the crosslinking monomer, the type and amount of porogen used, and the concentration of the free-radical initiator in the polymerization mixture.

By analogy to conventional sieving processes, the use of polymers with large pores is advantageous to promote rapid mass transfer through a porous polymer. In chromatography, this may be beneficial in a variety of preparative as well as analytical applications.

Two approaches are most frequently used for the preparation of porous polymers with very large pores. One approach is polymerization in the presence of a large volume fraction of a non-solvating diluent in the polymerization mixture. The other approach entails polymerization in the presence of a linear polymer porogen. So far, macroporous polymers have been almost exclusively produced in the shape of regular beads that are used as ion-exchange resins, chromatographic separation media, adsorbents etc. Therefore, studies directed towards the formation of macroporous structures have focused on materials prepared by suspension polymerization.

In search for enhanced and simpler chromatographic separation media, the polymerization of mixtures containing monomers and porogenic solvents has been done directly within the confines of a chromatographic column. See Frechet and Svec U.S. Pat. No. 5,334,310. It has been found that the material produced in accordance therewith, contains two sharply divided families of pores, i.e. large channels and more conventional small diffusive pores. This has been confirmed by examination of the material's unusual pore size distribution curve.

Because the plug columns are essentially a single molded polymer monolith traversed by large channels and permeated by small pores, their hydrodynamic properties are excellent. They are unlike any existing separation medium based on packed polymer beads because flow through the plug column does not involve any interstitial space but results entirely from the existence of the through channels built into the porous polymer monolith. Therefore, high rates of mass transfer can be used. Despite the high flow rates and steep gradients, separations using these plug columns are remarkably effective. The continuous polymer plug media afford excellent resolution in the separation of proteins, peptides and small molecules.

The continuous macroporous polymer plug of U.S. Pat. No. 5,334,310 is typically prepared as a homogeneously porous material that originates from a single polymerization mixture. In other words, one plug contains only one pore size distribution profile and only one composition and one type of functionality. In order to obtain different pore sizes and functionalities within one tube, a plurality of different plugs are used. Therefore, it would be a substantial advantage to develop a process that can be used to produce a single plug with gradients of pore size distributions and/or chemistries that would also be of use in a variety of applications including liquid chromatography.

DISCLOSURE OF THE INVENTION

Accordingly, the present invention is directed to a porous polymeric material having a porous polymer matrix in the form of an integral body with a first end and a second end, said porous polymer matrix having a property gradient extending from the first end of the integral body to the second end thereof. The property gradient is generally a pore size distribution gradient, a chemical composition gradient, or a combination of the two.

The present invention is also directed to a process for making such a porous polymeric material. In the process, the porous polymeric material is formed in a mold such as a stationary tube, thereby forming a shaped integral body. Most preferably, the body is generally cylindrical and referred to as a plug useful in a separation apparatus, such as a chromatographic separation column. The external conditions accompanying the polymerization within a stationary mold are quite different from those found in a conventional suspension polymerization process. First, only the organic mixture phase is present in the mold. Therefore, interfacial tension between the aqueous and organic phases, characteristic of a suspension process, is absent. Moreover, in contrast to the droplets that revolve in the aqueous phase as a result of stirring, the contents of the tube generally do not move during the polymerization.

In the process of the present invention, the polymerization rate, time, and temperature are used to control the pore size distribution. The polymerization rate depends on the concentration of the free radical initiator and on the reaction temperature. The shorter the polymerization time or the lower the initiator concentration and/or the lower the polymerization temperature, the larger the pores which are produced. The lower limit of the polymerization temperature depends on the decomposition rate of the specific free-radical initiator used. These effects are useful in practice because they allow control of the pore size distribution of an integral body without having to change the composition of the polymerization mixture.

Pore size distribution is used herein to refer to the presence of pores of different sizes. The actual distribution of the pores will depend upon the specific system produced. Examples of the pore size distribution curves that can result from the present invention are provided in the Figures. The actual profiles were measured by mercury porosimetry, although other techniques may be used. The profiles typically exhibit one or more maxima, i.e. peaks, that represent the pores with the largest volumes. The numerical values for the size of those pores in different materials can be obtained from pore size distribution curves and the numbers directly compared. It is also possible to calculate an average pore size from the experimental data and to compare the average pore sizes of different materials.

In the process of the present invention, an organic phase containing generally both monovinyl and divinyl monomers, an initiator, and a porogenic solvent is disposed in a stationary mold. The free-radical initiator decomposes at a particular temperature and the initiating radicals start the polymerization process in solution. The polymers that are formed by the polymerization precipitate in the reaction medium after becoming insoluble as a result of both their crosslinking and the porogen. In the process, the monomers are thermodynamically better solvation agents for the polymer than the porogen. Therefore, the precipitated insoluble gel-like species (nuclei) become swollen with the monomers that are still present in the surrounding liquid. The polymerization then continues both in solution and within the swollen nuclei. Polymerization within the latter is kinetically preferred because the local concentration of the monomers is higher in the individual swollen nuclei than in the surrounding solution. Branched or even crosslinked polymer molecules, that can still be formed in the solution, are captured by the growing nuclei and further increase in size. The crosslinked character of the nuclei prevents them from mutual penetration and from the complete loss of their individuality through coalescence. The nuclei, enlarged by the continuing polymerization, associate in clusters being held together by polymer chains that crosslink the neighboring nuclei.

The solid nuclei, or their clusters, generally have a higher density than the polymerization mixture. Therefore, in the absence of mixing, as prevails when polymerization occurs within a mold and if the overall rate of polymerization is slow, the solid nuclei or their clusters can sediment and accumulate at the lower end of the mold while a liquid polymerization mixture remains on the top of the formed solid polymer phase.

The unstirred nuclei and their clusters sediment to the lower end of the mold and form a very loose, highly porous and less organized structure early on during the polymerization. This structure contains very large pores and the nuclei retain a great deal of their individuality. As the nuclei contact one another, they become joined by some growing polymer chains and the loose structure becomes fixed in place. As a result, the integral body formed maintains its shape and does not fall apart, even after removal from the mold.

The polymerization process may then continue both in the mixture that is pooled at the top of the porous material, as well as in the mixture that is still present within the swollen very large pores of the early porous material already formed, resulting in the formation of some new nuclei.

It is also within the present invention to use temperature changes during a polymerization to fine-tune the overall porosity of an integral body and to prepare a porous polymeric material with a pore size distribution gradient. For example, the polymerization process can be conducted at a first temperature to a point at which the polymer body occupies substantially all of the space of the mold and there is no longer a pool of liquid at the top of the polymer body but while there is still polymerization mixture within the very large pores. Changing the polymerization temperature at this point will result in the formation of a porous material which has a porosity profile that is an overlap of the porosity profiles of the material prepared at a lower temperature and the material prepared at a higher temperature.

In other situations, the polymerization temperature can be changed while there is still a pool of unpolymerized mixture at the top of a formed porous polymer body. If a porous material is formed by polymerization at a first temperature to yield a first pore size distribution profile and, while unpolymerized mixture remains atop the material with the first profile, the temperature is changed to a second temperature, the remaining unpolymerized mixture will have a second pore size distribution profile and will predominantly occupy the space above the first profile material. The resultant gradient of pore size distribution is a stepwise gradient with one pore size distribution being present towards a first end of the body and another pore size distribution being present at the other end thereof.

Alternatively, the temperature can be changed continuously during the polymerization reaction to generate a porous material having a continuous axial gradient of pore size distribution.

Still another alternative involves the removal of the residual liquid polymerization mixture either (i) only from the liquid phase above the solid phase of a porous polymer or (ii) the liquid phase above the solid phase and also from within the pores of the solid phase porous material before the polymerization is completed, and replacing it with a chemically different liquid phase polymerization mixture. The polymerization can then be restarted and form a chemical composition gradient porous material. If the polymerization continues at the same temperature, only a chemical gradient will be produced. However, if polymerization continues at (or is later changed to) a different temperature, both a chemical and a pore size gradient will be produced.

Still alternatively, when there is polymerization mixture remaining within the pores of a body, the polymerization mixture can be removed from those pores to form a gradient. In this case, the polymerization process is conducted up to a point at which a porous material with very large pores has formed and the liquid polymerization mixture remaining in these pores is forced out of the pores using gravity, centrifugation, pressure, or vacuum. Under these conditions, the time during which the polymerization mixture resides in one end of the porous body will be different from the time the mixture resides at the other end and there will be continuous change between the two ends. Since pore size distribution depends on polymerization time, this process results in the formation of a porous material with a continuous gradient of pore size distribution.

The porous polymeric materials with a gradient of porosity and/or chemistry of the present invention are useful in chromatography, electrophoresis, separation catalysis, adsorption, diagnostics, sample preparation, environmental analyses, solid phase extraction and molecular recognition.

DETAILED DESCRIPTION OF THE PREFERRED EMBODIMENTS

The porous polymeric materials of the present invention contain a gradient, such as a pore size distribution gradient, which may be either continuous or stepwise. A continuous gradient changes substantially continuously in a direction extending from a first end to the second end of the porous polymeric body. While a stepwise gradient changes in one or more recognizable individual steps with a porous body. For a continuous pore size distribution gradient, the average pore size will likely range from about 50 to about 15,000 nm, preferably from about 400 to 5,000 nm, and more preferably from about 600 to 1,500 nm. In the case of a step-wise gradient, the porous polymeric material body generally contains two or more sections of different pore size distribution. The porous material may also contain a combination of at least one continuous gradient and at least one step-wise gradient. Alternatively the porous material may contain a combination of at least two step-wise gradients.

For example, in the case of a cylindrical plug body, the lower end of the plug body may contain one pore size distribution, the middle portion another pore size distribution and the other end of the plug body still another pore size distribution. The number of regions of different pore size distributions will, of course, be limited by the length of the body. Generally, a body having a length of about 10 cm may have from about 2 to 4 different pore size distribution regions. Generally, the difference between the average pore size in one portion and the average pore size in an adjacent portion of the same body is of from about 50 to 500 nm for a material to contain a stepwise pore size gradient. In a porous polymeric body having a continuous gradient, the range of average pore sizes is generally of from about 50 to 15,000 nm.

In addition to a pore size distribution gradient the porous polymeric material of the present invention may have a chemical composition gradient. This gradient may be present in addition to the pore size distribution gradient or instead of the pore size distribution gradient. Like the pore size distribution gradient, the chemical composition gradient may be stepwise. A stepwise gradient is exemplified by one portion of the polymer body such as the lower end having one chemical composition and the other end having a completely different composition. As will be discussed hereinafter, the process of the present invention allows for the formation of an unlimited number of different chemical composition regions in a porous polymer body. However, a polymer body having 2 to 4 different chemical compositions disposed in a stepwise gradient is presently the most practical. Another type of chemical composition gradient is wherein one region of the polymer body contains two types of chemical compositions with the adjacent region containing only one chemical composition.

The polymeric body of the present invention may be in any form or shape depending, of course, on the particular end use of the body. A particularly preferred form is a cylindrical plug for use in a chromatographic column. A plug of this type will be used as the separation media in the column through which a material sample passes through. Such a plug is generally greater than about 5 mm in thickness, distinguishing it from a membrane. The overall dimensions will, of course, depend upon the size of the column. Generally, the plug will have a cross-sectional area of at least about 10 μm$^2$ and a thickness or length of from about 5 to 200 or more mm.

The process used to produce the integral porous polymeric body of the present invention will depend on what type of property gradient is desired. However, no matter what type of gradient is desired, each process variation begins by preparing a polymerization mixture. A suitable polymerization mixture is one which contains at least a monovinyl monomer, a polyvinyl monomer, an initiator and a porogenic solvent. In addition to these components, the polymerization mixture may also contain a monovinyl monomer and conventional polymerization additives, such as chain transfer agents, soluble polymers, chealating agents and the like.

Suitable polyvinyl monomers include divinylbenzene, divinylnaphthalene, divinylpyridine, alkylene bis-acrylamides, alkylene bis-methacrylamides, alkylene dimethacrylates, such as ethylene dimethacrylate, hydroxyalkylene dimethacrylates such as ethylene dimethacrylate, hydroxyalkylene diacrylates, oligoethylene glycol dimethacrylates, oligoethylene glycol diacrylates, vinyl esters of polycarboxylic acids, divinyl ether, and mixtures of any such suitable polyvinyl monomers. The alkylene groups generally contain about 2 to 6 carbon atoms.

Monovinyl monomers which may be used include styrene, ring substituted styrene wherein the substituents include such as alkyl groups having about 2 to 20 carbon atoms, sulfonic, phosphonic, carboxyl, amino, and nitro groups, acrylamides and methacrylamides, vinylnaphthalene, acrylates, methacrylates such as glycidyl methacrylate, vinylacetate, vinylpyrrolidone, and mixtures thereof. The polyvinyl monomer or polyvinyl monomer plus the vinyl monomer are generally present in the polymerization mixture in an amount of from about 10 to 80, more preferably in an amount of from about 30 to 60% by weight.

The porogen that is used may be selected from a variety of different types of materials. For example, suitable porogens include solutions of soluble polymers, aliphatic hydrocarbons, aromatic hydrocarbons, esters, alcohols, ketones, ethers and mixtures thereof. The porogen is generally present in the polymerization mixture in an amount of from about 20 to 90, more preferably in an amount of from about 40 to 70% by weight.

Any conventional polymerization initiator may initiate polymerization. Examples of suitable initiators for vinyl polymerizations are free radical generators which include peroxides such as benzoyl peroxide, lauroyl peroxide and peroxodisulfate as well as azo compounds such as azobisisobutyronitrite. The initiator is generally present in the polymerization mixture in an amount of from about 0.1 to 5% by weight of the monomers.

Prior to adding the polymerization mixture to a mold, the mixture is generally deaerated by conventional means, such as by bubbling an inert gas, such as nitrogen, into the mixture for a sufficient period of time to remove oxygen present in the mixture. Once the polymerization mixture is prepared and deaerated, it is added to a mold sealed at both ends by suitable fittings.

Once the mixture is in the mold, polymerization is carried out conventionally incorporating the various process step variations to achieve a property gradient. Polymerization generally occurs at a temperature of from about 50° to 90° C. for a period of from about 6 to 24 hours, depending on the initiator and monomers used and the property gradient desired. Polymerization is preferably carried out in an inert atmosphere such as nitrogen or argon. While heating may be supplied by conventional means, it is presently preferred to immerse the sealed mold containing the polymerization mixture into a heated bath or air oven.

After polymerization is complete, the solid macroporous polymer plug is washed with a suitable solvent and the porogen in the polymer is dissolved. Suitable solvents include methanol, ethanol, tetrahydrofuran, dimethylsulfoxide, dimethylformamide, and toluene. The washing process may be done in stages. For example, the washing process may involve washing with a solvent, then with water and then a solvent again, or by continuous washing with a solvent. The washing step is preferably carried out by pumping the solvent through the tube filled with the macroporous polymer.

Adding a polymerization mixture to a tube or mold is the first step in all of the process variations of the present invention. At this point in the process, there are variations depending upon the type of property gradient desired.

When a continuous pore size distribution gradient is desired, polymerization is initiated at a relatively low temperature so as to start polymerization slowly. The specific temperature will depend upon the specifics of the polymerization mixture including the initiator being used. For any particular polymerization mixture, the starting temperature is readily known to the skilled artisan. For example, in a mixture comprising azobisisobutyronitrile, glycidyl methacrylate, ethylene dimethacrylate, cyclohexanol, and dodecanol polymerization at a slow rate can be initiated at a low temperature of about 55° C. At a low temperature after about 12 hours, polymerization will produce a body that contains relatively large pores having a maximum diameter of about 1,100 nm. To achieve a continuous pore size distribution gradient, the temperature is gradually increased preferably in about 5° C. increments and not kept at a single temperature for a long period of time. The time at any one temperature will depend on the rate of polymerization. Thus, if polymerization begins at 55° C., as the body of porous polymer having a relatively large pore size distribution begins to form and settle to the bottom of the polymerization mixture the temperature should be elevated and the average pore size will decrease. As more of the polymer body forms the temperature may again be elevated. This process continues until the complete polymer body is formed and substantially no liquid phase remains. The resulting polymer body will possess a continuous pore size distribution gradient which gradient decreases in average pore size from one end of the body to the other end.

To produce a polymer body with a stepwise gradient, the process is carried out by polymerizing at different temperatures over defined periods of time to produce regions of distinctly different pore size distributions. While the number of distinct regions in a polymer body is theoretically unlimited, practical consideration such as body length and the length of time it takes to polymerize a specific polymerization mixture set practical limits of from about 2 to 4 distinct regions of different pore size distribution, more preferably 2 to 3 distinct regions of different pore size distributions.

A chemical composition gradient may be achieved in addition to or without a pore size distribution gradient by carrying out certain process steps. First to obtain a stepwise chemical composition gradient, during the polymerization process, but prior to the completion of polymerization and the formation of a solid polymer body, there exists a stage at which a solid body is formed and is disposed in the mold at the bottom thereof with the unpolymerized liquid phase remaining thereabove and in the pores of the solid body. At this point, the liquid above the body is removed and replaced with a chemically different polymerization mixture. Polymerization is then continued to either completion or to a point wherein a liquid phase above the solid phase polymer body still remains. The liquid phase is then removed and replaced by a chemically different polymerization mixture and polymerization is continued to completion or the removal and replacement procedure may again repeated so long as there remains a liquid phase above the solid polymer body. In this manner, an integral polymer body with 2 or more separate regions of different chemical compositions is obtained.

A chemical composition gradient can also be achieved by removing not only the liquid on top of the polymer body formed but also the liquid in the pores of the body and replacing the total liquid with a different chemical composition which both fills the pores of the polymer body already formed and the region above the polymer body. Polymerization is then continued and resulting in a portion of the polymer body being composed of two different compositions and the adjacent portion having a different overall composition, which can be either a single polymer composition (provided liquid is not again removed from the pores in this region in a subsequent process step), or a mixed polymer composition (if in a subsequent process step liquid is removed from the pores in the second portion and replaced with a chemically different polymerization mixture which is subsequently polymerized). Again, while there is no theoretical limit to the number of times the liquid phase can be replaced it is presently preferred to carry out the replacement step 1 to 2 times.

The present invention will now be described with reference to the following examples in which all parts and percents are by weight unless otherwise specified.

EXAMPLE 1

A continuous plug was prepared by in situ polymerization within the confines of a stainless steel tube of a 50×8 mm i.d. chromatographic column. The 40:60 vol % mixture of monomers (glycidyl methacrylate and ethylene dimethacrylate, 60:40 vol %) and porogenic diluents (cyclohexanol and dodecanol, 90:10 vol %) in which azobisisobutyronitrile (1% w/v with respect to monomers) was dissolved, was pumped with nitrogen for 15 minutes. The stainless steel tube was sealed at one end with a rubber septum covered with a piece of polyethylene film and filled with the above mixture. The column was sealed at the other end again with a rubber septum covered with a piece of polyethylene film and the polymerization was allowed to proceed at 55° C. for 1 hour. The column was removed from the bath and cooled quickly in an ice-water mixture. The seals were removed, the column was provided with fittings and attached to the HPLC system. After the polymerization was completed, tetrahydrofuran (100 ml) was pumped through the plug at a flow rate of 0.5 ml/min to remove the alcohols and other soluble compounds present in the polymer plug.

Figure 1:
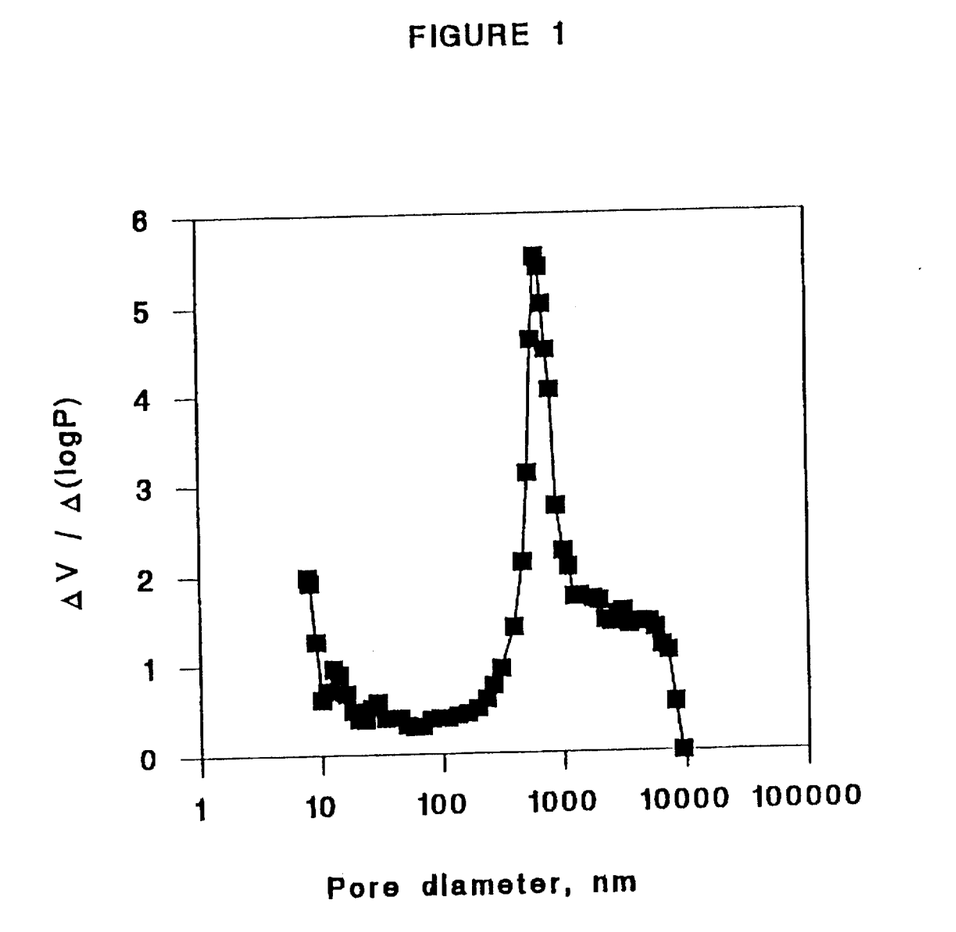
FIG. 1 shows a pore size distribution profile of a poly-(glycidyl methacrylate-co-ethylene dimethacrylate) rod prepared by a 1 hr polymerization at a temperature of 55° C. (■). Polymerization mixture: glycidyl methacrylate 24%, ethylene dimethacrylate 16%, cyclohexanol 54%, dodecanol 6%, and azobisisobutyronitrile (1% w/v with respect to monomers).

Once the washing was complete the column was opened at the bottom and the porous polymer was removed from the tube using solvent pressure. The plug was dried at a temperature of 50° C. The polymerization conversion was 16% as calculated from the weight of the dry plug. Mercury intrusion porosimetry measurement shown in FIG. 1 shows a distinct maximum at 618 nm. However, the plug also contains a substantial amount of very large pores with diameter up to 10,000 nm. The total pore volume of the plug determined by mercury porosimetry is 3.769 ml/g and the specific surface area determined by BET method is 523.8 $m^2/g$.

EXAMPLE 2

Figure 2:
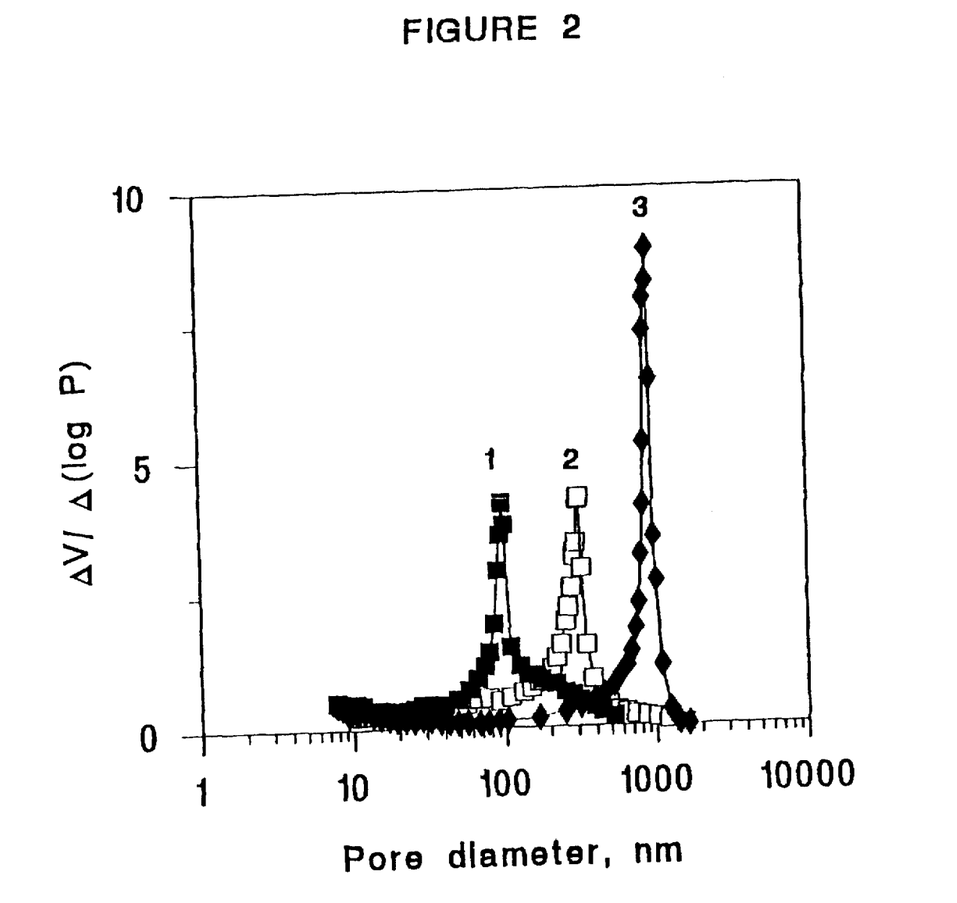
FIG. 2 shows a pore size distribution profile of a poly-(glycidyl methacrylate-co-ethylene dimethacrylate) rod prepared by a 12 hr polymerization at a temperature of 55° C. (■), 12 hr at 70° C. (♦) and at a temperature increased during the polymerization from 50° to 70° C. in steps by 5° C. lasting 1 hr each and kept at 70° C. for another 4 hrs (□). Polymerization mixture: glycidyl methacrylate 24%, ethylene dimethacrylate 16%, cyclohexanol 54%, dodecanol 6%, and azobisisobutyronitrile (1% w/v with respect to monomers)

A continuous plug was prepared by a process essentially identical to that used in Example 1 except for different temperature conditions. The results of mercury porosimetry measurements are shown in FIG. 2. In addition to rods prepared by a polymerization lasting 12 hours at fixed temperatures of 55° C. (curve 1) and 70° C. (curve 3), FIG. 2 also includes a curve obtained for a plug prepared using a step-gradient of polymerization temperature. The temperature was increased during polymerization from 50° to 70° C. in 5° C. steps of one hour each. The plug was then kept at the final temperature of 70° C. for another 4 hours. The maximum of the distribution curve in this plug prepared in a step gradient of temperature is between the maxima for the rods prepared at 55° and 70 ° C. ( curve 2) .

EXAMPLE 3

Figure 3:
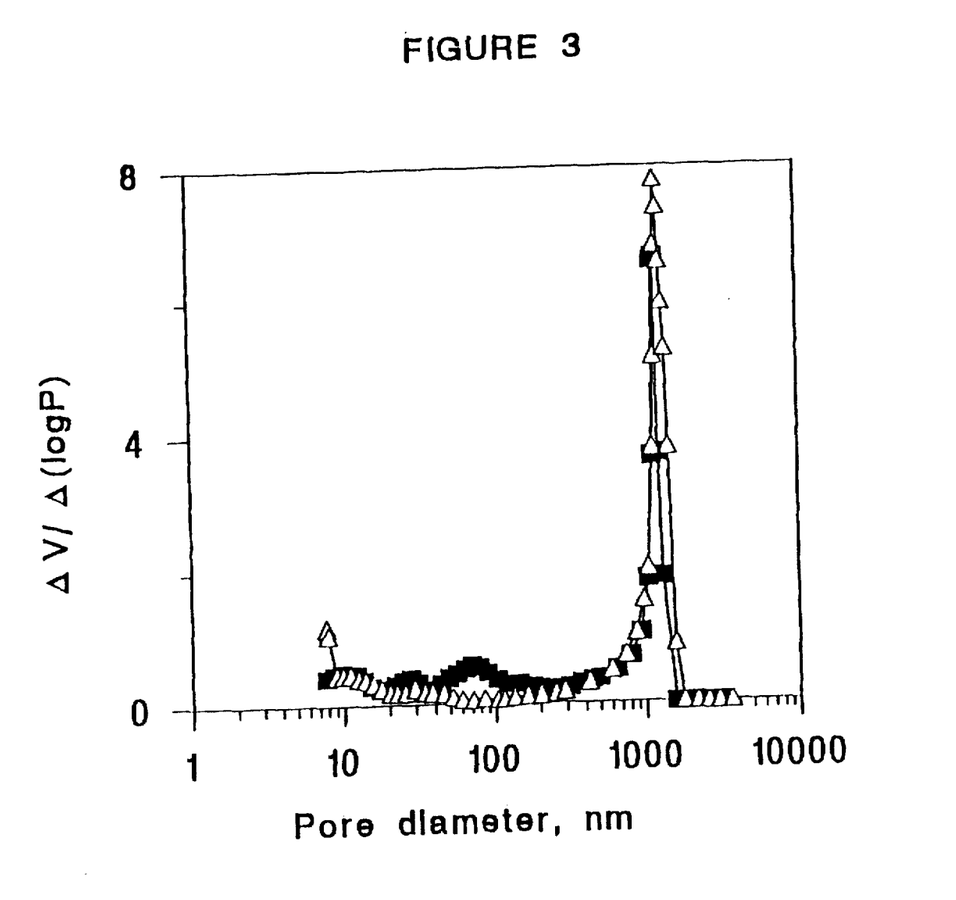
FIG. 3 shows a pore size distribution profile of the top (■) and the bottom part (Δ) of a poly-(glycidyl methacrylate-co-ethylene dimethacrylate) rod polymerized 1 hr at a temperature of 55° C. followed by 14 hr at 70° C. Polymerization mixture: glycidyl methacrylate 24%, ethylene dimethacrylate 16%, cyclohexanol 54%, dodecanol 6%, and azobisisobutyronitrile (1% w/v with respect to monomers).
Figure 4A:
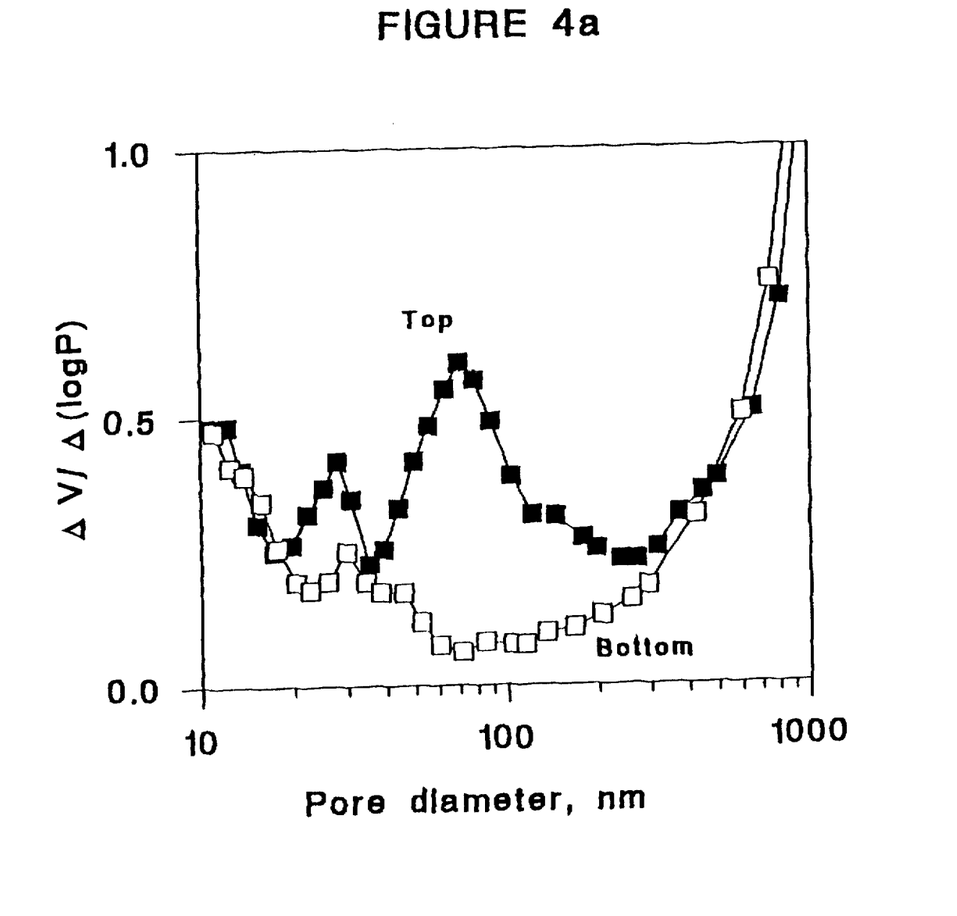
FIGS. 4a and 4b show a pore size distribution profile of (a) top (■) and bottom part (□) of a poly(glycidyl methacrylate-coethylene dimethacrylate) rod polymerized 1 hr at a temperature of 55° C. followed by 14 hr at 70° C.; (b) a rod polymerized 1 hr at a temperature of 55° C. (■), and a rod polymerized 14 hr at 70° C. (□). Polymerization mixture: glycidyl methacrylate 24%, ethylene dimethacrylate 16%, cyclohexanol 54%, dodecanol 6%, and azobisisobutyronitrile (1% w/v with respect to monomers).
Figure 4B:
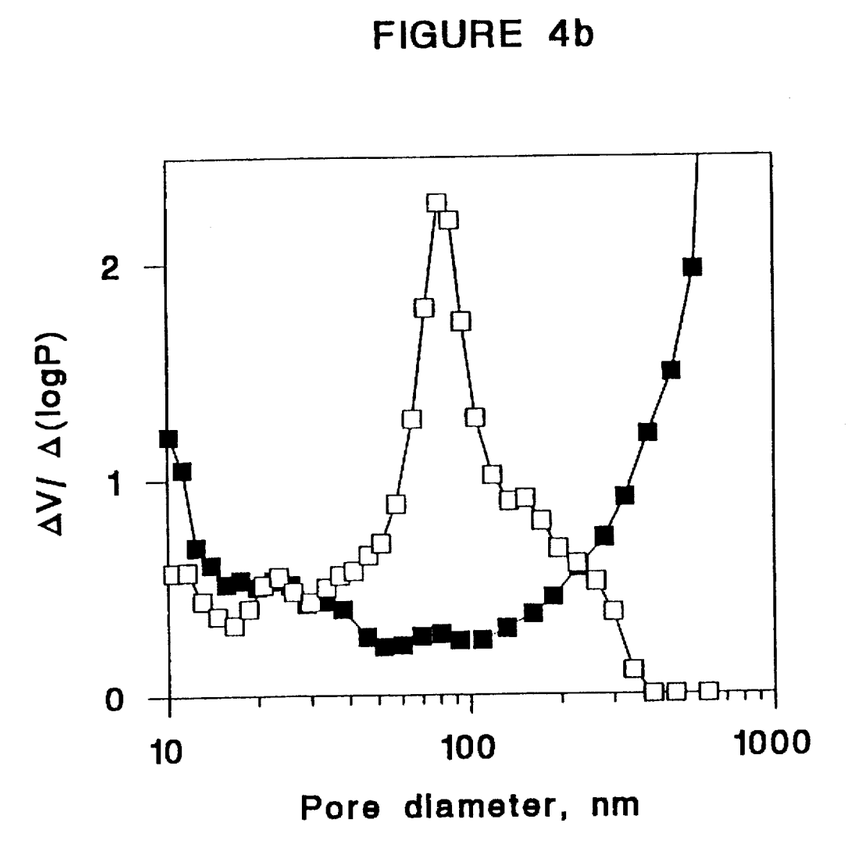

A plug with an axial gradient of porosity was prepared by a polymerization process similar to that used in Example 1. The polymerization proceeded at 55° C. for 1 hour. After this polymerization time, a pool of liquid polymerization mixture still remained both above the top of the solid plug and within its large pores. This polymerization mixture was then polymerized by raising the temperature to 70° C. for 14 hours while the tube stood vertically in the bath. FIG. 3 shows that a different porosity profile is achieved at the two extremities of the plug. While both parts of the plug contain large pores centered near 1200 nm in diameter, the top of the plug which is formed in the later stages of the polymerization (opened triangles) contains a very significant volume of smaller pores. FIG. 4 shows a magnification of the same porosity profiles for the top and bottom portions of the plug. While the volume of pores in the range 30–200 nm is only 6.7% in the bottom part, it accounts for a remarkable 25.5% at the top with a distinct maximum centered at about 80 nm. For comparison, FIG. 4b shows the striking similarity of the magnified overlay of porosity profiles for plug prepared by a polymerization at 55° C. for one hour, then processed, and for a plug obtained after the standard polymerization time 14 hours at 70° C.

EXAMPLE 4

A continuous plug with an internal gradient of chemistry is prepared by polymerization in a 50×8 mm i.d. chromatographic column. Two polymerization mixtures are prepared. The first one consisted of a 40:60 vol % mixture of monomers (glycidyl methacrylate and ethylene dimethacrylate in a ratio of 3:2 vol/vol) and porogenic diluents (cyclohexanol and dodecanol, 90:10 vol %) in which azobisisobutyronitrile (1% w/v with respect to monomers) is dissolved, while the second one contained a 40:60 vol. % mixture of different monomers (styrene and divinylbenzene (80% divinyl monomer), 50:50 vol. %) and porogenic solvent (dodecanol) in which again azobisisobutyronitrile (1% w/v with respect to monomers) is dissolved.

The mixture is purged with nitrogen for 15 minutes. The stainless steel tube is sealed at one end with a piece of polyethylene film covering a rubber septum and then it is filled with the first mixture. The column is sealed at the other end again with a piece of polyethylene film covering a rubber septum and the polymerization is allowed to proceed at 55° C. for 3 hours. This reaction time is sufficient to produce a very porous plug that fills the tube completely. The plug is removed from the bath and cooled quickly in an ice-water mixture. The seals are removed and the plug is provided with fittings, then attached to the HPLC system. The second monomer mixture (10 ml) is then pumped through the column at a flow rate of 0.5 ml/min to replace the remaining unpolymerized first monomer mixture that remained located within the large pores of the primary plug. Once filled with the new monomer mixture, the column is detached from the chromatograph, sealed at both ends and the polymerization is continued for 24 hours at 70° C.

The seals are removed again, the column is provided with fittings and reattached to the HPLC system. Tetrahydrofuran (100 ml) is pumped through the plug at a flow rate of 0.5 ml/min to remove the soluble compounds present in the polymer plug after the polymerization is completed.

EXAMPLE 5

A continuous plug with both internal and longitudinal gradients of chemistry is prepared by polymerization in a 100×4 mm i.d. chromatographic column. Two polymerization mixtures are prepared. The first one consisted of the 40:60 vol % mixture of monomers (glycidyl methacrylate and ethylene dimethacrylate, 60:40 vol %) and porogenic diluents (cyclohexanol and dodecanol, 90:10 vol %) in which azobisisobutyronitrile (1% w/v with respect to monomers) is dissolved while the second one contained a 40:60 vol. % mixture of different monomers (octyl methacrylate and ethylene dimethacrylate, 60:40 vol. %) and porogenic solvent (cyclohexanol and dodecanol, 90:10 vol. %) in which again azobisisobutyronitrile (1% w/v with respect to monomers) is dissolved.

The mixtures are purged with nitrogen for 15 minutes. The stainless steel tube is sealed at one end with a piece of polyethylene film covering a rubber septum and filled with the first mixture. The column is sealed at the other end again with a rubber septum, covered with a piece of polyethylene film, and the polymerization is allowed to proceed at 55° C. for 1 hour. After this time of polymerization, a very porous plug with a porosity profile similar to that of FIG. 1 is formed that had a length corresponding to about two thirds the tube length. The column is removed from the bath and cooled quickly in an ice-water mixture. The seals are removed, the column is provided with fittings and attached to the HPLC system. The second mixture (5 ml) is pumped through the plug at a flow rate of 0.1 ml/min to replace the portion of the first monomer mixture that remained unpolymerized and that is located within the large pores of the primary plug as well as above the plug. Once filled with the new monomer mixture, the column is detached from the chromatograph, sealed at both ends and the polymerization is continued for 10 hours at 55° C.

The seals are removed again, the column is provided with fittings and reattached to the HPLC system. Tetrahydrofuran (100 ml) is pumped through the plug at a flow rate of 0.5 ml/min to remove the soluble compounds present in the polymer plug after the polymerization is completed.

The continuous plug contains a chemical gradient: (i) a first end having a porous copolymer rich in octyl methacrylate and ethylene dimethacrylate, (ii) the other end having a glycidyl methacrylate-ethylene dimethacrylate matrix filled with some octyl methacrylate-ethylene dimethacrylate copolymer, and (iii) a gradient therebetween changing from one composition to the other.

EXAMPLE 6

A continuous plug with a longitudinal gradient of chemistry prepared by polymerization in a 150×8 mm i.d. chromatograph column. The two polymerization mixtures are the same as in the Example 5. The stainless steel tube is sealed at one end and filled with the first mixture. The column is sealed at the other end and the polymerization is allowed to proceed at 55° C. for 1 hour. A very porous plug with a porosity profile similar to that of FIG. 1 is formed occupying again only about two thirds the tube length. The column is removed from the bath and cooled quickly in an ice-water mixture. The seal at the upper end is removed and the residual liquid is removed by a syringe. The empty space is filled with the second polymerization mixture, the column sealed again and the polymerization continued for 10 hours at 55° C.

After the polymerization is completed, the seals from both ends are removed, the column is provided with fittings and attached to the HPLC system. Tetrahydrofuran (100 ml) is pumped through the plug at a flow rate of 0.5 ml/min to remove the soluble compounds present in the polymer plug after the polymerization is completed.

The continuous plug contains a chemical gradient: (i) a first end having a porous copolymer rich in octyl methacrylate and ethylene dimethacrylate, (ii) the other end having a glycidyl methacrylate-ethylene dimethacrylate matrix, and (iii) a gradient therebetween changing from one composition to the other.

EXAMPLE 7

A continuous plug with a continuous porosity gradient is prepared by an in situ polymerization within a 100×15 mm o.d. glass tube. The 40:60 vol % mixture of monomers (glycidyl methacrylate and ethylene dimethacrylate, 60:40 vol %) and porogenic diluents (cyclohexanol and dodecanol, 90:10 vol %) in which azobisisobutyronitrile (1% w/v with respect to monomers) is dissolved, and purged with nitrogen for 15 minutes. The glass tube is sealed at one end with a rubber septum covered with a piece of polyethylene film and filled to one half of its height with the above mixture. The column is sealed at the other end again with a rubber septum covered with a piece of polyethylene film and the polymerization is allowed to proceed at 55° C. for 2 hours. The tube is rotated 180° in the bath and vacuum is applied in the empty space using an injection needle pricked through the septum. The polymerizaton continues under these conditions for another 10 hours.

The tube is removed from the bath and cooled to the ambient temperature. The seals are removed, the plug removed from the tube and washed with tetrahydrofuran. This single plug contains a continuous gradient of porosity.

What is claimed is:

1. A macroporous material comprising a permanently porous polymeric matrix in the form of a non-gelled dried integral body having a thickness about 5 mm or more and having a first end and a second end disposed longitudinally from the first end, said macroporous material having an average pore size of from about 50 nm–15,000 nm, said permanently porous polymeric matrix having a property gradient extending from the first end of the integral body to the second end thereof, wherein the property gradient is selected from the group consisting of pore size distribution, chemical composition, and a combination thereof.

2. The porous polymeric material of claim 1, wherein the property gradient is a pore size distribution gradient.

3. The porous polymeric material of claim 2, wherein the gradient is continuous.

4. The porous polymeric material of claim 2, wherein the gradient is stepwise.

5. The porous polymeric material of claim 1, wherein the property gradient is a chemical composition gradient.

6. The porous polymeric material of claim 5, wherein the gradient is stepwise.

7. The porous polymeric material of claim 5, wherein the gradient is continuous.

8. The porous polymeric material of claim 5, wherein the material is composed of two different polymeric materials.

9. The porous polymeric material of claim 1, wherein the property gradient is a combination of a pore size distribution gradient and a chemical composition gradient.

10. The porous polymeric material of claim 1, wherein the polymeric material comprises a copolymer of a polyvinyl monomer and a monovinyl monomer.

11. The porous polymeric of claim 10, wherein the monovinyl monomer is selected from the group consisting of styrene, substituted styrene, acrylamides, methacrylamides, vinylnaphthalene, acrylates, methacrylates, vinylacetate, vinylpyrolidone, and mixtures thereof, wherein when styrene is substituted the substituents are selected from the group consisting of alkyl having about 2 to 20 carbon atoms, sulfonic, phosphonic, carboxyl, amino, and nitro groups.

12. The porous polymeric material of claim 10, wherein the polyvinyl monomer is selected from the group consisting of divinylbenzene, divinylnaphthalene, divinylpyridine, alkylene bis-acrylamides, alkylene bis-methacrylamides, alkylenalkylene, dimethacrylates, alkylenediacrylates, hydroxyalkylene dimethacrylates, hydroxyalkylene diacrylates, oligoethylene glycol dimethacrylates, oligoethylene glycol diacrylates, vinyl and allyl esters of polycarboxylic acids, divinyl ether and mixtures thereof.

* * * * *